United States Patent [19]

Dickerhoff et al.

[11] Patent Number: 4,997,429

[45] Date of Patent: Mar. 5, 1991

[54] ENTERAL BOTTLE CAP WITH VENT VALVE

[75] Inventors: Scott D. Dickerhoff, Manchester; Alan B. Ranford, Creve Coeur; David R. Swisher; Eugene F. Schrader, both of St. Louis; Raymond O. Bodicky, Oakville; Ronald Crouther, Chesterfield, all of Mo.

[73] Assignee: Sherwood Medical Company, St. Louis, Mo.

[21] Appl. No.: 290,790

[22] Filed: Dec. 28, 1988

[51] Int. Cl.⁵ .............................................. A61B 19/00
[52] U.S. Cl. .................................... 604/411; 604/405; 604/406
[58] Field of Search ................. 604/85, 405, 406, 407, 604/411–414; 128/214; 222/189, 83

[56] References Cited

U.S. PATENT DOCUMENTS

| | | | |
|---|---|---|---|
| 2,668,533 | 2/1954 | Evans | 604/405 |
| 2,770,234 | 11/1956 | Nesset et al. | 604/405 |
| 2,812,117 | 11/1957 | Butkus et al. | 222/189 |
| 2,852,024 | 9/1958 | Ryan | 604/251 |
| 3,542,240 | 11/1970 | Solowey | 222/83 |
| 4,215,690 | 8/1980 | Oreopoulos et al. | 604/411 |
| 4,262,671 | 4/1981 | Kersten | 604/411 X |
| 4,332,247 | 6/1982 | Mittleman et al. | 604/82 |
| 4,505,709 | 3/1985 | Froning et al. | 604/411 |
| 4,534,758 | 8/1985 | Akers et al. | 604/85 |
| 4,588,403 | 5/1986 | Weiss et al. | 604/411 |

FOREIGN PATENT DOCUMENTS 2105695  3/1983  United Kingdom ................ 604/406

*Primary Examiner*—Robert A. Hafer
*Assistant Examiner*—Lynda M. Cofsky
*Attorney, Agent, or Firm*—Andrew J. Beck; Montgomery W. Smith; Richard D. Allison

[57] ABSTRACT

A connection component suitable for use with an enteral fluid delivery set wherein the connection component consists of a threaded cap having a projecting spike thereon to penetrate and deform a foil diaphragm on the fluid container and further including an air passageway having a flexible member therein to allow filtered air to flow into the fluid container while preventing the flow of fluid from the fluid container through the air passageway.

13 Claims, 2 Drawing Sheets

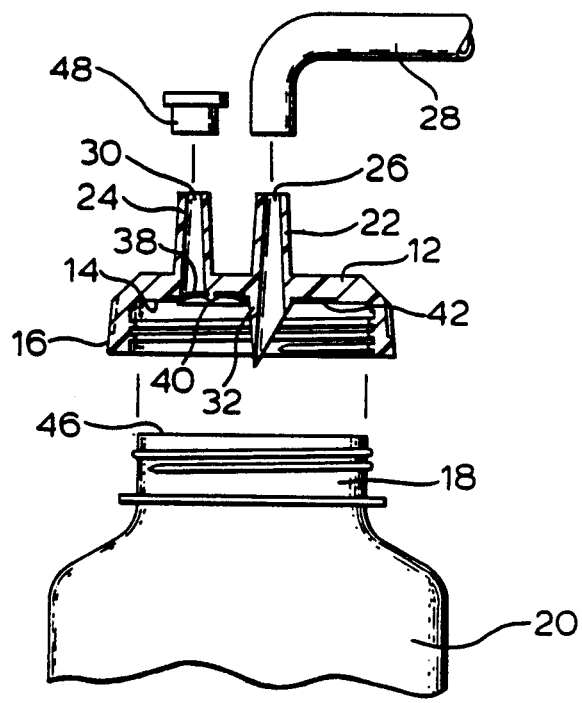
FIG. 4
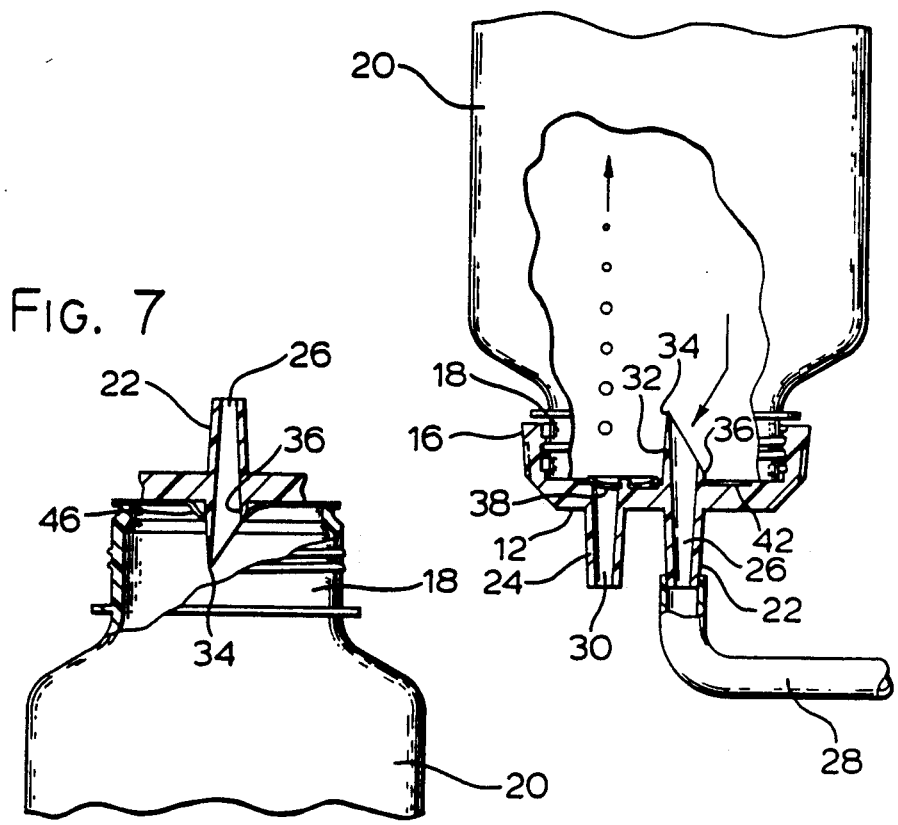
FIG. 5
FIG. 7

ENTERAL BOTTLE CAP WITH VENT VALVE

FIELD OF THE INVENTION

The present invention relates to a connection component designed to be mounted on a tubing assembly for connecting the tubing assembly to a prefilled, foil-sealed container, and in particular to a connection component which includes a spike for penetrating the foil seal and an air vent having a flexible membrane therein. The present invention is also generally related to a copending application filed on Aug. 30, 1988, Ser. No. 239,044 now U.S. Pat. No. 4,888,008 granted Dec. 19, 1989, which is a continuation of an application filed on Mar. 3, 1987, Ser. No. 021,181 entitled "Vented Spike Connection Component" assigned to Sherwood Medical Company.

BACKGROUND OF THE INVENTION

In an enteral fluid delivery system for a patient, there is a need to provide a connecting component which will effect a quick connection of the fluid delivery set to a prefilled, foil-sealed container containing enteral fluid. In these fluid delivery systems, the connecting component is preferably a cap, which replaces the shipping cap on the prefilled container when the container is connected to the fluid delivery set for administration of the enteral fluid to the patient. The connecting component preferably includes a means for perforating the foil diaphragm on the container during attachment of the fluid delivery set to the container to simplify the assembly of the delivery system. It is further desireable that the connecting component provide a means to allow air to vent into the container as the enteral fluid flows from the container. This venting means should be designed to allow filtered air to flow into the container while preventing the air from flowing into and through the fluid passageway. Additionally, the venting means must prevent the passage of enteral fluid from the container through the air passageway.

One approach is illustrated in U.S. Pat. No. 3,542,240, issued to Solowey on Nov. 24, 1970. The first embodiment of Solowey illustrates the use of a single, centrally positioned projection designed to puncture the diaphragm of the container. The projection includes parallel air and liquid passageways therein to allow vented air to flow into the container while the fluid is administered to the patient. Additionally, Solowey illustrates the use of a check valve consisting of a steel ball and coil spring moveably positioned within the air passageway. Finally, the Solowey device includes a circular flange on the bottle which engages a flexible sleeve on the cap to prevent the removal of the cap during the operation of the administration set. Another embodiment of Solowey illustrates the use of a pair of parallel, spaced apart air and liquid passageways therein.

The present invention seeks to provide a connection component for effecting a quick and reliable coupling between the fluid delivery set and the prefilled, sealed container. The present invention minimizes the potential for contamination of the container by providing an efficient means for puncturing the foil diaphragm of the container while simultaneously tearing the diaphragm to create a passageway therein to allow for the flow of vented filtered air therethrough.

SUMMARY OF THE INVENTION

An advantage of the present invention is that the connection component will puncture the protective diaphragm on the enteral fluid containing container as the connection component is being attached to the top of the container.

Another advantage of the present invention is that the air passageway is spaced apart from the liquid passageway to prevent the vented air from flowing into the liquid passageway.

Another advantage of the present invention is that the air passageway includes a flexible membrane therein to allow filtered air to flow into the enteral fluid container while preventing enteral fluid from leaking out of the container through the air passageway.

Another advantage of the present invention is that the spike member is offset from the center of the cap so that as the cap is attached to the container, the spike member will tear the diaphragm to create a passageway therein for the vented air.

Another advantage of the present invention is that the opening of the air passageway is recessed from the diaphragm on the container to ensure that the diaphragm does not obstruct the flow of air from the air passageway.

The present invention provides a connection component which consists primarily of a cap specifically designed for attachment to the top opening of an enteral fluid containing container. The cap includes a spike member which extends inwardly from the body of the cap toward the container. The spike member is offset from the center of the cap body and includes a fluid passageway therein to allow for fluid communication between the container and the fluid delivery set. The cap further includes an air vent offset from the center of the cap body and oriented opposite the opening of the spike member. A flexible membrane is positioned adjacent to the inner opening of the air vent to allow the passage of air into the container while preventing enteral fluid from leaking out of the container through the air vent.

BRIEF DESCRIPTION OF THE DRAWINGS

FIG. 4 is an exploded perspective view, partly in section taken along lines 4—4 of FIG. 6;

FIG. 5 is a partial cut-away view illustrating the connection component attached to the container and tubing of the present invention.

FIG. 7 is a partial cut-away view illustrating the connection component piercing the foil diaphragm of the prefilled container.

DETAILED DESCRIPTION OF THE PREFERRED EMBODIMENT

Figure 1:
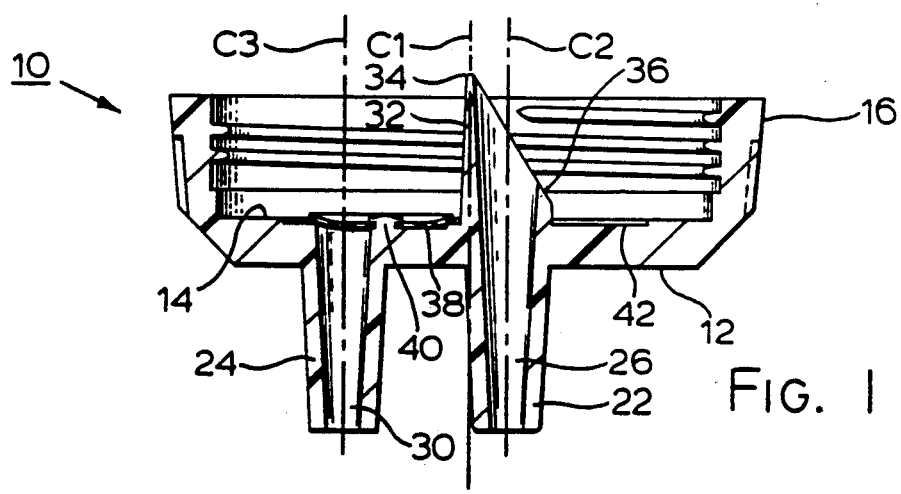
FIG. 1 is an enlarged cross-sectional view of the connection component of the present invention.
Figure 2:
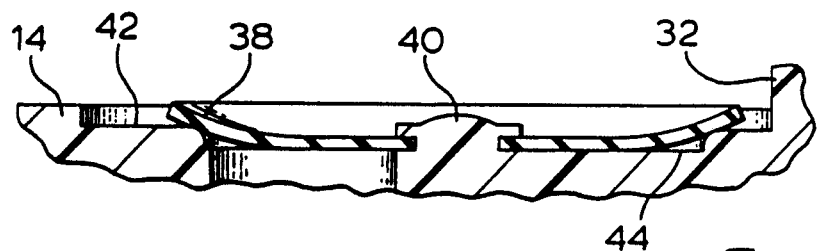
FIG. 2 is an enlarged cross-sectional view of the flexible disk and air passageway of the present invention shown in FIG. 1.

One form of the present invention is illustrated in the drawings and is described generally herein as a connection component or cap 10. The cap 10 includes a top surface 12, a bottom inside surface 14 and a rim 16 adapted to be removably mounted on the neck 18 of a prefilled container 20. The cap 10 is preferably of a one-piece construction formed from a molded plastic such as styrene.

The top surface 12 includes a pair of cylindrically shaped first and second members, 22 and 24, respectively, extending outwardly from the top surface 12 of the cap 10. Both members, 22 and 24, are offset from the central axis C1 of the cap 10, with the second member 24 being positioned midway between the central axis C1 of the cap 10 and one side of the cap 10, while the first member 22 is offset slightly from the central axis C1 of the cap 10. The first member 22 includes an internal liquid passageway 26 and is adapted to be attached to a plastic tubing 28 which, along with the cap 10, forms part of the fluid delivery set. The second member 24 includes an internal air passageway 30 and a standard filter (not shown) which allows filtered air to flow into the prefilled container 20.

The bottom inner surface 14 of the cap 10 includes a spike member 32 which is formed by truncating the cylindrically shaped first member 22 at an angle starting at a location near the bottom inside surface 14 of the cap 10 and extending to an apex 34. The apex 34 of the spike member 32 extends beyond the bottom edge of the rim 16. The apex 34 is aligned on the bottom inside surface 14 of the cap 10 adjacent to the central axis C1 of the cap 10 while the opposing side 36 of the spike member 32 is positioned away from the central axis C1 of the cap 10 and in alignment with the apex 34 and central axis C1. The liquid passageway 26 in the first member 22 extends through spike member 32 to allow fluid communication between the tubing 28 and the container 20.

The bottom inside surface 14 of the cap 10 further includes first and second recesses, 42 and 44 respectively, and a flexible disk 38. The first recess 42 extends along nearly the entire bottom inside surface 14 of the cap 10 to provide a spaced apart relationship between the bottom inside surface 14 of the cap 10 and the diaphragm 46 on the container 20. The second recess 44 is positioned generally between the apex 34 of the spike member 32 and the rim 16 of the cap 10. The air passageway 30 of the second member 24 opens into the second recess 44 between the center of the second recess 44 and the rim 16 of the cap 10. The flexible disk 38 is retained in the second recess 44 by a spike shaped retainer 40. The retainer 40 is melted thermally or ultrasonically to retain the flexible disk 38 in the second recess 44. The flexible disk 38 is preferably constructed of a soft plastic or elastomeric, non-porous, material and is designed to overlap the rim of the second recess 44.

As illustrated in the drawings, the cap 10 has a central axis designated as C1, about which the cap 10 is rotated for attachment to the container 20. As further illustrated in the drawings, first and second members 22 and 24, respectively, are both offset from the central axis C1 and extend upwardly from the top surface 12 of the cap 10. Additionally, the apex 34 of spike member 32 on the bottom inside surface 14 of the cap 10 is oriented so that the opening of the liquid passageway 26 faces away from the opening of the second member 24. The center of the liquid passageway 26 in the first member 22 is designated in the drawings as axis C2. Axis C2 of the liquid passageway 26 is offset from the central axis C1 by approximately 0.1 inch (2.5 mm). The center of the air passageway 30 in the second member 24 is designated in the drawings as axis C3. Axis C3 of the air passageway 30 is offset from the axis C2 of the liquid passageway 26 by approximately 0.5 inch (12.7 mm). This aligned separation of the respective passageways, along with the orientation of the apex 34 on the spike member 32 effectively prevents air bubbles from flowing directly into the liquid passageway 26 of the first member 22.

Figure 3:
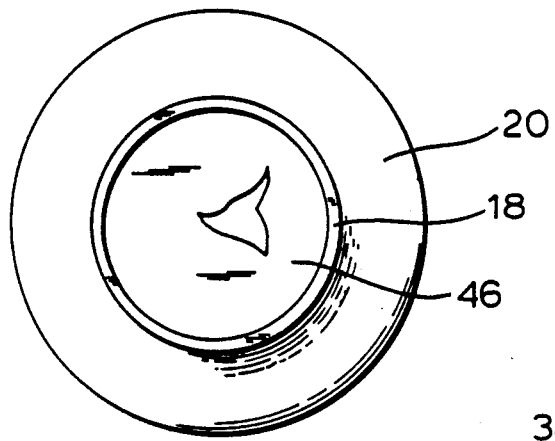
FIG. 3 is a top view of the foil diaphragm of the prefilled container after the diaphragm has been penetrated by the connection component of the present invention.
Figure 6:
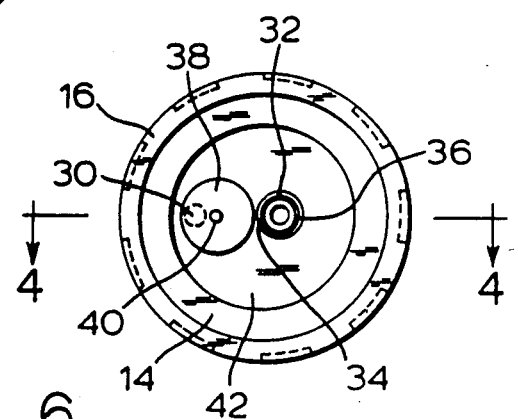
FIG. 6 is a bottom view of the connection component of the present invention.

With this preferred orientation of the spike member 32 and the first and second recesses, 42 and 44 respectively, of the present invention, air is drawn into the air passageway 30 of the second member 24 without significant obstruction by the diaphragm 46. As illustrated in FIG. 3, the diaphragm 46 is deformed and torn by the offset spike member 32 to provide an opening in the diaphragm 46 which is sufficiently extended to permit fluid to flow freely through the liquid passageway 26 in the first member 22 into the tubing 28 and to allow air to flow freely through the second member 24 into the container 20. The first recess 42 ensures that the flexible disk 38 will be spaced apart from the diaphragm 46 a sufficient distance so that the flexible disk 38 is allowed to flex in response to the passage of air from the air passageway 30 into the container 20. The second recess 44 causes the flexible disk 38 to be biased slightly towards the inside of the container 20 and ensures that the air bubbles are deflected away from the liquid passageway 26.

The cap 10 of the present invention forms an integral part of an improved fluid delivery set. The enteral fluid containing container 20 is typically delivered with a specially designed shipping cap which must be removed prior to the attachment of the cap 10 on the container 20. In the preferred embodiment, the cap 10 is threaded onto the neck 18 of the container 20. As the cap 10 is threaded onto the container 20, the spike member 32 pierces the protective diaphragm 46 in the manner illustrated in FIG. 3. Next, the tubing 28 is attached to the first member 22 on the top surface 12 of the cap 10. The container 20 is then inverted and the air is removed from the tubing 28. Finally, the safety cap 48 is removed from the second member 24 to allow the air passageway 30 to communicate through a filter (not shown) between the atmosphere and the interior of the container 20. The delivery set is now ready to administer the enteral fluid to the patient.

In operation, the enteral fluid flows from the container 20 through the liquid passageway 26 into the tubing 28. As this occurs, filtered air is drawn into the air passageway 30 through the second member 24. The air will flow through the air passageway 30 and bubble past the flexible disk 38. By extending the flexible disk 38 beyond the perimeter of the second recess 44, the flexible disk 38 operates as a flexible barrier against the bottom inside surface 14 of the cap 10 to direct the air bubbles away from the opening of the liquid passageway 26 in the container 20. The flexible disk 38 also prevents the loss of enteral fluid from the container 20 through the air passageway 30 by pressing against the second recess 44 whenever the pressure inside the container 20 is greater than the atmospheric pressure.

The detailed description of the preferred embodiment of the invention having been set forth herein for the purpose of explaining the principles thereof, it is known that there may be modifications, variations or changes in the invention without departing from the proper scope of the invention as defined by the claims attached hereto.

What is claimed is:

1. A connection component for connecting a fluid delivery set to a fluid containing container having a top opening having a tearable diaphragm and a threaded connection thereon wherein the connection component comprises:

a cap shaped connection component including a circular body portion having top and bottom surfaces and a cylindrical rim portion extending in one axial direction therefrom and adapted to be threadedly received on the fluid containing container;

a projecting member having an outer diameter, a pointed apex and a lower angled opposing side wherein said apex on said projecting member extends downwardly from said bottom surface of said body portion beyond said rim portion and at least a portion of said projecting member is oriented offset from the horizontal center of said body portion, a fluid passageway passing through said body portion and substantially enclosed by said projecting member said fluid passageway having a fluid receiving opening which opens adjacent to said opposing side of said projecting member and wherein said apex is nearest to the horizontal center of said body portion and wherein said apex extends further from said body portion than said fluid receiving opening and said projecting member is adapted to tear the diaphragm on the container to form an opening therein that is larger than said diameter of said projecting member;

said body portion having an air passageway therein extending through said body portion and offset from the horizontal center of said body portion and wherein said air passageway is oriented opposite said fluid receiving opening with respect to the horizontal center of said body portion; and a movable member in flow communication with said air passageway to selectively allow air to flow into said container while preventing fluid from passing therethrough.

2. The connecting component of claim 1, wherein said projecting member is cylindrical and has an apex formed by an angled plane beginning near said body portion and extending in the same axial direction as said rim portion extends from said body portion to the apex of said projected member located at the horizontal center of said body portion.

3. A connection component for connecting a fluid delivery set to a fluid containing container having a top opening and a threaded connection thereon wherein the connection component comprises:

a cap shaped connection component including a circular body portion having top and bottom surfaces and a cylindrical rim portion extending in one axial direction therefrom;

a projecting member having a pointed apex and a lower opposing side wherein said projecting member extends downwardly from the bottom surface of said body portion beyond said rim portion, and is oriented offset from the horizontal center of said body portion, said projecting member having a fluid passageway therein passing through said body portion and said fluid passageway and having a fluid receiving opening which opens adjacent to the lower opposing side of said projecting member and wherein said apex is nearest to the horizontal center of said body portion and wherein said apex extends further from said body portion than the fluid receiving opening;

said body portion having an air passageway therein extending through said body portion and offset from the horizontal center of said body portion and wherein said air passageway is oriented opposite said projecting member with respect to the horizontal center of said body portion;

a flexible member in flow communication with said air passageway to selectively allow air to flow into said container while preventing fluid from passing therethrough; and wherein said air passageway includes said flexible member in flow communication with said air passageway and wherein said flexible member is on said bottom surface of said body portion and said flexible member is in a first recess on the bottom surface of said body portion.

4. The connecting component of claim 3, wherein said flexible member further comprises a circular flexible disk wherein said flexible disk is attached to said body portion by a retainer which retains said flexible disk on the bottom surface of said body portion.

5. The connecting component of claim 4, wherein said flexible member is substantially displaced in a second recess on the bottom surface of said body portion.

6. A fluid delivery system consisting of a fluid containing container having a top opening, a tearable protective diaphragm covering said opening and a connection neck for receiving a connection component thereon and a tubing set, wherein said connection component comprises:

a cap shaped member including a circular body portion having top and bottom surfaces and a cylindrical rim portion extending downwardly from said bottom surface, said rim portion adapted to threadedly receive the neck connection on the container therein;

a generally cylindrical and pointed projecting member having a predetermined diameter and extending downwardly from said bottom surface of said body portion, said projecting member having an apex thereon and being generally laterally offset from the horizontal center of said body portion and said projecting member having a fluid receiving passageway substantially enclosed therein, said passageway extending through said body portion and having a fluid receiving opening therein which opens generally along said projecting member and said apex extends beyond the fluid receiving opening and is adapted to tear the diaphragm of the container to form an opening in the diaphragm larger than the diameter of said projecting member upon the connection of said cap shaped member to the container;

an air passageway in said body portion spaced laterally from the horizontal center of said body portion on the side of said body portion laterally opposite to said passageway and wherein said apex on said projecting member is adjacent the horizontal center of said body portion; and wherein said air passageway extends upwardly from said bottom surface and beyond said top surface through said body portion and includes a movable member in flow communication therewith to allow air to selectively flow through said air passageway into the container while preventing the flow of liquid therethrough.

7. The connection component of claim 6, wherein said movable member comprises a recessed and flexible disk member which is affixed to said bottom surface of said body portion adjacent to said air passageway.

8. The connection component of claim 6, wherein said movable member comprises a recessed nonporous flexible member in flow communication with said air passageway to selectively allow air to flow from said air passageway into the container while preventing the flow of liquid therethrough.

9. The connection component of claim 6, wherein said top surface of said cap shaped member includes first and second cylindrical members thereon wherein said first cylindrical member is in flow communication with said projecting member and is adapted for the connection of a tubing set thereon to allow fluid to flow therethrough.

10. The connection component of claim 9, wherein said second cylindrical member includes a filter member and in flow communication with said air passageway and is adapted for the passage of atmospheric air therethrough.

11. A fluid delivery system consisting of a fluid containing container having a top opening, a pierceable protective diaphragm covering said opening and a connection neck for receiving a connection component thereon and a tubing set, wherein said connection component comprises:
a cap shaped member including a circular body portion having top and bottom surfaces and a cylindrical rim portion extending downwardly from said bottom surface, said rim portion adapted to threadedly receive the neck connection on the container therein;
a pointed projecting member having a predetermined diameter and extending downwardly from said bottom surface of said body portion, said projecting member having an apex and being generally laterally offset from the horizontal center of said body portion and said projecting member having a fluid receiving passageway therein and said passageway extending through said body portion and said passageway having a fluid receiving opening therein which opens on the bottom surface of said projecting member, said projection member being cylindrical and having an end on said apex such that said end extends beyond the fluid receiving opening and pierces the diaphragm of the container to form an opening in the diaphragm larger than the diameter of said projecting member upon the connection of said cap shaped member to said
an air passageway in said body portion spaced laterally from the horizontal center of said body portion on the side of the body portion laterally opposite to said projecting member;
wherein said air passageway extends from said bottom surface and beyond said top surface through said body portion and includes a flexible member in flow communication therewith to allow air to selectively flow through said air passageway into said container while preventing the flow of liquid therethrough; and
wherein the body portion of said connection component includes a recess adjacent to said air passageway wherein said flexible member substantially overlaps said recess to resiliently block the flow of liquid from said container through said air passageway.

12. The connection component of claim 11, wherein said body portion of the connection component includes a further recess therein to space said flexible member apart from the diaphragm of the container when said cap shaped member is attached to the container.

13. A connecting component arranged for attachment to the opening of a fluid container, said connecting component including a body portion having a top surface, a bottom rim surface and a bottom inside surface for covering the container opening, a projecting member extending from said bottom inside surface toward the container from a position on said bottom inside surface to a location beyond said bottom rim surface and at least a portion of which is spaced apart from the horizontal center of said body portion, an apex on said projecting member generally aligned with the horizontal center of said body portion, a fluid channel passing through said body portion wherein said fluid channel has a fluid receiving opening therein substantially enclosed by said projecting member and wherein said connection component further includes an air passageway having top and bottom ends wherein said bottom end is recessed from said bottom inside surface of said connecting component and wherein said air passageway extends through said body portion and is spaced apart from said projecting member and oriented generally opposite and spaced apart from said fluid channel with respect to the horizontal center of said body portion and wherein said air passageway includes a flow restricting means in flow communication therewith to selectively allow air to flow therethrough, and wherein said flow restricting means of said air passageway comprises a flexible disk member in flow communication with said bottom end of said air passageway and substantially positioned in said recess on said bottom inside surface of said body portion.

* * * * *